(12) United States Patent
Pigamo et al.

(10) Patent No.: US 10,633,312 B2
(45) Date of Patent: Apr. 28, 2020

(54) METHOD FOR PURIFYING AND DRYING A HYDROFLUOROOLEFIN STREAM

(71) Applicant: Arkema France, Colombes (FR)

(72) Inventors: Anne Pigamo, Francheville (FR); Dominique Deur-Bert, Charly (FR); Laurent Wendlinger, Soucieu en Jarrest (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 15/761,543

(22) PCT Filed: Sep. 19, 2016

(86) PCT No.: PCT/EP2016/072142
§ 371 (c)(1),
(2) Date: Mar. 20, 2018

(87) PCT Pub. No.: WO2017/050686
PCT Pub. Date: Mar. 30, 2017

(65) Prior Publication Data
US 2018/0346396 A1 Dec. 6, 2018

(30) Foreign Application Priority Data
Sep. 24, 2015 (FR) .................................. 15 59002

(51) Int. Cl.
*C07C 17/389* (2006.01)
*C07C 21/18* (2006.01)

(52) U.S. Cl.
CPC .................................. *C07C 17/389* (2013.01)

(58) Field of Classification Search
CPC .................................................. C07C 17/389
See application file for complete search history.

(56) References Cited

U.S. PATENT DOCUMENTS

| 8,252,964 B2* | 8/2012 | Devic | C07C 17/389 570/177 |
| 2010/0162738 A1* | 7/2010 | Low | B01D 53/261 62/101 |
| 2015/0011803 A1* | 1/2015 | Imura | B01J 20/18 570/135 |
| 2016/0272560 A1* | 9/2016 | Chiu | C07C 17/389 |

FOREIGN PATENT DOCUMENTS

| EP | 2 796 439 | 10/2014 |
| GB | 2 439 209 | 12/2007 |
| JP | 2012-001495 | 1/2012 |
| WO | WO-2010/001025 | 1/2010 |
| WO | WO-2015/125877 | 8/2015 |

OTHER PUBLICATIONS

Kazuyoshi, K. et al. Patent No. JP2012001495, Jan. 5, 2012, pp. 1-12; English translation (Year: 2012).*
Specification of the U.S. Appl. No. 62/135,282 (Year: 2015).*
International Search Report dated Dec. 6, 2016 for PCT/EP2016/072142.

* cited by examiner

*Primary Examiner* — Medhanit W Bahta
(74) *Attorney, Agent, or Firm* — NK Patent Law

(57) ABSTRACT

The invention concerns a method for purifying and drying a hydrofluoroolefin stream comprising a hydrofluoroolefin, water and impurities composed of halogenated carbon compounds, characterised in that said stream is brought into contact with an adsorbent and in that the purification and the drying processes are carried out simultaneously in one and the same step, said hydrofluoroolefin being a compound of formula (I): $CX_1X_2=CX_3X_4X_5X_6$ in which each $X_i$ (i ranging from 1 to 6) represents, independently of one another, a hydrogen atom or a chlorine or fluorine atom, it being understood that at least one of the $X_i$'s represents a fluorine atom.

13 Claims, No Drawings

METHOD FOR PURIFYING AND DRYING A HYDROFLUOROOLEFIN STREAM

CROSS-REFERENCE TO RELATED APPLICATIONS

This application is a U.S. National Stage application of International Application No. PCT/EP2016/072142, filed Sep. 19, 2016, which claims the benefit of French Application No. 1559002, filed Sep. 24, 2015.

FIELD OF THE INVENTION

The present invention concerns a method for purifying and drying a stream of hydrofluoroolefins using an adsorbent. The present invention also concerns the use of an adsorbent for simultaneous drying and purifying of a stream of hydrofluoroolefins.

TECHNICAL BACKGROUND

The Montreal Protocol for protection of the ozone layer has led to discontinued use of chlorofluorocarbons (CFCs). Compounds less harsh on the ozone layer have therefore replaced chlorofluorocarbons, such as hydrofluorocarbons (HFCs). However, these compounds make a relatively large contribution towards the greenhouse effect. Efficient replacement compounds have therefore been researched having both a low ODP (Ozone Depletion Potential) coefficient and low GWP (Global Warming Potential) coefficient. Hydrofluoroolefins (HFOs) have been identified as desirable alternatives on account of their low ODP and GWP values.

Hydrofluorocarbons (HFCs) and in particular hydrofluoroolefins (HFOs), such as 2,3,3,3-tetrafluoro-1-propene (HFO-1234yf) are compounds with known properties as refrigerants and heat-transfer fluids, as fire-extinguishing and propellant agents, foaming agents, swelling agents, dielectric gases, polymerisation or monomer medium, as carrier fluids, agents for abrasives, drying agents and fluids for energy production units. Unlike CFCs and HCFCs, that are potentially dangerous for the ozone layer, HFOs do not contain chlorine and therefore do not give rise to problems for the ozone layer when used.

It is known to produce hydrofluoroolefins or hydrofluorocarbons via fluorination of hydrochloroolefins or hydrochlorocarbons in particular. This fluorination is generally a catalytic fluorination using hydrofluoric acid as fluorinating agent.

This type of production method generally requires washing steps in columns provided for this purpose (water or basic aqueous solution) to remove certain undesirable products (residual HF in particular). These washing steps may lead to hydrofluoroolefin compositions comprising water and/or moisture.

As a result, methods for producing hydrofluoroolefin compositions generally comprise one or more drying steps after the washing steps, to obtain streams that are anhydrous or substantially anhydrous before subsequent treatment steps. The conventional methods used for drying are for example the use of a compound having dehydrating properties such as calcium chloride, magnesium sulfate, sodium sulfate, calcium sulfate, potassium hydroxide or calcium oxide. Other well-known methods involve the use of a molecular sieve, silica gel or activated carbon.

In addition, the methods generally used for producing hydrofluoroolefin compositions lead to the formation of by-products (impurities) of hydrocarbon compound type, requiring subsequent purification steps.

Document JP2013241390 describes a method for purifying a stream comprising 2,3,3,3-tetrafluoro-1-propene (1234yf) obtained by pyrolysis. Document WO 2013/115048 describes a method for purifying a stream of 1-chloro-3,3,3-trifluoropropene (1233zd) using a zeolite. In this document, separate steps of washing and drying are applied before it is possible to carry out the purification step.

There is therefore a need to simplify the method for producing hydrofluoroolefin compositions, for example by limiting the number of steps whilst maintaining an efficient method that affords satisfactory yield, in particular for industrial applications.

The present invention sets out to propose a novel method for purifying and drying hydrofluoroolefin compositions allowing both drying to be obtained and the removal of impurities of hydrocarbon type, in particular saturated halogenated hydrocarbons. Therefore, in the method of the invention, purification and drying are conducted simultaneously in one same step.

SUMMARY OF THE INVENTION

The invention first concerns a method for purifying and drying a hydrofluoroolefin stream comprising a hydrofluoroolefin, water and impurities based on halogenated carbon compounds, characterized in that said stream is placed in contact with an adsorbent and in that purification and drying are performed in one same step, said hydrofluoroolefin being a compound of formula (I): $CX_1X_2=CX_3CX_4X_5X_6$ wherein each $X_i$ (i ranging from 1 to 6) is independently of one another a hydrogen atom or a chlorine or fluorine atom, provided that at least one of Xi is a fluorine atom.

According to one embodiment, the hydrofluoroolefin stream comprising a hydrofluoroolefin, water and impurities comprises at least 50% by weight, preferably at least 70% by weight, preferably at least 90%, preferably at least 95% by weight, preferably at least 98% by weight, preferably at least 99% by weight of at least one same hydrofluoroolefin, relative to the total weight of the stream comprising a hydrofluoroolefin, water and impurities.

According to one embodiment of the invention, the adsorbent is a membrane and/or molecular sieves, preferably molecular sieves.

Preferably, the molecular sieves have a pore opening of mean diameter ranging from 3 to 15 Å, preferably from 5 to 10 Å.

Preferably, the molecular sieves are zeolites of type X or A.

According to one embodiment of the invention, the impurities based on halogenated carbon compounds comprise at least one compound selected from chloromethane (F40), fluoromethane (F41), difluoromethane (F32), tetrafluoromethane (F14), trifluoromethane (F23), 1,1,1-trifluoroethane (F143a), 1,1-difluoroethane (F152a), pentafluoroethane (F125), chloropentafluoroethane (F115), 1,1,1,2-tetrafluoroethane (F134a), pentafluoropropane (F245), monochlorotetrafluoropropene (F244), 1,3,3,3-tetrafluoropropene (F1234ze) isomer E or Z, 3,3,3-trifluoropropene (1243zf), 1,2,3,3,3-pentafluoropropene (F1225ye), 3,3,3-trifluoropropyne, 1,3-dichloro-3,3-difluoropropene (F1232zd), 1,1-dichloro-3,3-difluoropropene (F1232za), 1,1-dichloro-1,3,3-trifluoropropane (F243fc), cis isomer of 1-chloro-3,3,3-trifluoropropene (Z-1233zd).

According to one embodiment of the invention the hydrofluoroolefin stream, before being placed in contact with the adsorbent, comprises from 10 to 10,000 ppm by mass of water and/or the hydrofluoroolefin stream before being placed in contact with the adsorbent comprises from 500 to 8,000 ppm by mass of impurities.

According to one particular embodiment of the invention, the hydrofluoroolefin stream is a stream of 1234yf. According to this embodiment, the adsorbent is preferably a zeolite of type A having a pore diameter ranging from 3 Å to 6 Å. According to this embodiment, the impurities are preferably selected from chloromethane (F40), tetrafluoromethane (F14), trifluoromethane (F23), 1,1-difluoro-ethane (F152a), alone or in a mixture.

According to another particular embodiment of the invention, the hydrofluoroolefin stream is a stream of 1233zd, preferably a stream of 1233zd of E configuration. According to this embodiment, the adsorbent is preferably a zeolite of type X having a pore diameter ranging from 8 Å to 12 Å. According to this embodiment, the impurities are preferably selected from pentafluoropropane (F245), 1,3,3,3-tetrafluoropropene (F1234ze), 1,3-dichloro-3,3-difluoropropene (F1232zd), 1,1-dichloro-3,3-difluoropropene (F1232za), 1,1-dichloro-1,3,3-trifluoropropane (F243fc), alone or in a mixture, preferably from pentafluoropropane (F245), 1,3,3,3-tetrafluoropropene (F1234ze), 1,3-dichloro-3,3-difluoropropene (F1232zd), 1,1-dichloro-3,3-difluoropropene (F1232za), 1,1-dichloro-1,3,3-trifluoropropane (F243fc), 1-chloro-3,3,3-trifluoropropene of Z configuration (Z-1233zd), alone or in a mixture.

The invention also concerns the use of an adsorbent for the simultaneous drying and purification of a hydrofluoroolefin stream comprising a hydrofluoroolefin, water and impurities based on halogenated carbon compounds, said hydrofluoroolefin being a compound of formula (I): $CX_1X_2\!=\!CX_3CX_4X_5X_6$ wherein each $X_i$ (i ranging from 1 to 6) is independently of one another a hydrogen atom or a chlorine or fluorine atom, provided that at least one of Xi is a fluorine atom.

The method of the invention is simple to implement, in particular on an industrial scale.

The method of the invention allows to obtain a hydrofluoroolefin composition having improved purity using a simplified process.

The method of the invention allows to dry and purify a hydrofluoroolefin stream in one and the same step.

The method of the invention is based on the surprising discovery that it is possible, in one and the same step, to dry and purify a hydrofluoroolefin stream using an adsorbent. Up until the present time, drying and purification were conducted in two different steps. It was generally recognised by those skilled in the art that in the presence of water or moisture, the adsorbent became saturated with this water or moisture and became unusable to carry out purification.

DESCRIPTION OF EMBODIMENTS OF THE INVENTION

The invention will now be described in more non limiting detail in the following description.

The present invention proposes a method for purifying and drying a hydrofluoroolefin comprising the contacting of a stream comprising a hydrofluoroolefin (species of interest), water and impurities based on halogenated compounds (differing from the species of interest) with an adsorbent.

By "hydrofluoroolefin", in the meaning of the present invention is meant a hydrocarbon compound comprising at least one unsaturation and at least one fluorine atom.

According to one embodiment, the hydrofluoroolefin comprises at least 3 fluorine atoms.

According to the invention, the hydrofluoroolefin is a compound of formula (I): $CX_1X_2\!=\!CX_3CX_4X_5X_6$ wherein each $X_i$ (i ranging from 1 to 6) is independently of one another a hydrogen atom or a chlorine or fluorine atom, provided that at least one of Xi is a fluorine atom.

According to one embodiment, the hydrofluoroolefin is selected from 1-chloro-3,3,3-trifluoropropene (1233zd) or 2,3,3,3-tetrafluoropropene (1234yf), preferably the hydrofluoroolefin is 1-chloro-3,3,3-trifluoropropene (1233zd).

According to one embodiment of the invention, the stream comprising a hydrofluoroolefin (species of interest), water and impurities, before being placed in contact with the adsorbent, comprises at least 50% by weight of at least one hydrofluoroolefin, preferably at least 70% by weight of at least one hydrofluoroolefin, more preferably at least 90% by weight of at least one hydrofluoroolefin, even at least 95% by weight of at least one hydrofluoroolefin or even at least 98% by weight of at least one hydrofluoroolefin, or at least 99% by weight of at least one hydrofluoroolefin relative to the total weight of the stream comprising a hydrofluoroolefin, water and impurities.

By "impurity", it is meant a species contained in the stream comprising a hydrofluoroolefin, water and impurities, in a minority amount, preferably in an amount of 5% by weight or less relative to the total weight of said stream. The impurity or impurities differ from the hydrofluoroolefin as species of interest.

The stream comprising a hydrofluoroolefin can be obtained using a process known to persons skilled in the art, for example using a process such as described in document US 2014/0296585 or document WO 2015/104517.

When producing hydrofluoroolefins, washing steps are often necessary and cause water or moisture to enter the washed hydrofluoroolefin stream. In addition, by-products (impurities) are also obtained during the reaction leading to the desired hydrofluoroolefin.

According to one embodiment the stream, comprising a hydrofluoroolefin, water and impurities based on halogenated compounds, comprises less than 5% of water and impurities based on halogenated compounds, preferably less than 3% of water and impurities based on halogenated compounds, more preferably less than 2% by weight of water and impurities based on halogenated compounds, advantageously less than 1% by weight of water and impurities based on halogenated compounds relative to the total weight of said stream.

The impurities are generally saturated or unsaturated, halogenated compounds e.g. halogenated compounds having one, two or three carbon atoms.

Among the halogenated impurities having one or two carbon atoms, mention can be made of chloromethane (F40), fluoromethane (F41), difluoromethane (F32), tetrafluoromethane (F14), trifluoromethane (F23), pentafluoroethane (F125), chloropentafluoroethane (F115), 1,1,1,2-tetrafluoroethane (F134a), 1,1,1-trifluoroethane (F143a) and 1,1-difluoroethane (F152a).

Other halogenated impurities having 3 carbon atoms may also be formed, such as pentafluoropropane (F245), monochlorotetrafluoropropene (F244), 1,3,3,3-tetrafluoropropene (F1234ze), 3,3,3-trifluoropropene (1243zf), 1,2,3,3,3-pentafluoropropene (F1225ye), 3,3,3-trifluoropropyne, 1,3-dichloro-3,3-difluoropropene (F1232zd), 1,1-dichloro-3,3-difluoropropene (F1232za) and 1,1-dichloro-1,3,3-trifluoropropane (F243fc).

If there exist two isomers, one of the isomers can be considered to be an impurity in relation to the other, mention being made in particular of the cis isomer of 1-chloro-3,3,3-trifluoropropene in a stream mostly containing trans-1-chloro-3,3,3-trifluoropropene, or the cis isomer of 1,3,3,3-tetrafluoropropene in a stream mostly containing trans-1,3,3,3-tetrafluoropropene.

With the method of the invention, it is possible to obtain a stream that is both enriched with hydrofluoroolefin, i.e. the molar proportion of hydrofluoroolefin (product of interest) in the initial stream before purification and drying is lower than the molar proportion of said hydrofluoroolefin in the stream after purification and is also depleted of impurities.

The stream comprising a hydrofluoroolefin, water and impurities based on halogenated compounds used in the method of the invention, may comprise before purification, for example:

from 10 to 10,000 ppm by weight of water, preferably from 50 to 8,000 ppm by weight of water; and from 500 to 8,000 ppm by weight, preferably from 1,000 to 6,000 ppm by weight of impurities based on halogenated compounds, relative to the total weight of the hydrofluoroolefin stream.

Preferably, the stream after purification and drying comprises from 5 to 100 ppm by mass of water and from 5 to 3,000 ppm by mass of impurities.

For example, the water may derive from a preceding washing step of the hydrofluoroolefin stream.

The purification method of the invention comprises placing the stream comprising the hydrofluoroolefin, water and impurities in contact with an adsorbent.

Preferably, the adsorbent is selected from a membrane and/or molecular sieves.

Preferably, the adsorbent is selected from molecular sieves.

Molecular sieves, also called synthetic zeolites, are chemical compounds widely used in industry as adsorbents, in particular for drying gases or liquids. They are metallic aluminosilicates having a three-dimensional crystalline structure formed of an assembly of tetrahedrons. These tetrahedrons are formed by four oxygen atoms occupying the apexes and surrounding either a silicon atom or an aluminium atom positioned in the centre. These structures generally contain cations to render the system electrically neutral, such as those derived from sodium potassium or calcium.

According to one embodiment of the invention, the adsorbent is a molecular sieve having a pore diameter ranging from 3 Å to 15 Å, preferably ranging from 5 Å to 10 Å.

Suitable molecular sieves are preferably those of type A and type X.

Regarding so-called type A molecular sieves, the tetrahedrons are assembled such that they form a truncated octahedron. These octahedrons are themselves arranged in simple cubic crystalline structure, forming a network with cavities having an approximate diameter of 11.5 Å. These cavities are accessible via openings or pores which may be partly blocked by cations. If these cations are derived from sodium, these cavities have an opening diameter of 4 Å, giving what is known has a "4 A" molecular sieve. The crystalline structure of said sieve can be represented by the following chemical formula: $Na_{12}[(AlO_2)_{12}(SiO_2)_{12}]\cdot XH_2O$ where X representing the number of water molecules belonging to the structure (crystallisation water) may reach 27, which represents 28.5% by weight of the anhydrous zeolite.

The size of the openings (or pores) may be modified however depending on the different types of molecular sieves. For example, via exchange of a large part of the sodium ions of a 4 Å molecular sieve by potassium ions, a 3 Å molecular sieve is obtained having a pore diameter of about 3 Å. A 5 Å molecular sieve is obtained by replacing the sodium ions by calcium ions, the effective pore diameter then being in the order of 5 Å. The elementary cell of the zeolite X is a tetrahedron the apexes of which are occupied by polyhedrons of same type as those contained in zeolite A, each being connected to four other polyhedrons by means of an octahedral sub-structure formed by a double-ring containing eight oxygen atoms. The centre of each edge is always occupied by an oxygen atom, whilst the silicon and aluminium atoms occupy the different apexes of the polyhedrons. The empirical formula has the structure $Na_{88}Al_{88}Si_{104}O_{384}\cdot 220H_2O$.

According to one embodiment of the invention, the hydrofluoroolefin stream is a stream of 2,3,3,3-tetrafluoropropene (1234yf) and the adsorbent is a zeolite of type A having a pore diameter ranging from 3 Å to 6 Å.

According to this embodiment, the invention allows the removal in one same step of the moisture or water as well as the organic impurities such as chloromethane (F40), tetrafluoromethane (F14), trifluoromethane (F23) or 1,1-difluoro-ethane (F152a), contained in the initial stream.

According to this embodiment, the initial hydrofluoroolefin stream may comprise from 90% to 99% by weight of 12,3,3,3-tetrafluoropropene (1234yf), from 0.05% to 3% by weight of water, from 0.05% to 3% by weight of chloromethane (F40), from 0.05% to 3% by weight of tetrafluoromethane (F14), from 0.05% to 3% by weight of trifluoromethane (F23) and from 0.05% to 3% by weight of 1,1-difluoro-ethane (F152a), relative to the total weight of the hydrofluoroolefin stream.

According to another embodiment of the invention, the hydrofluoroolefin stream is a stream of 1-chloro-3,3,3-trifluoropropene (1233zd) and the adsorbent is a zeolite of type X having a pore diameter ranging from 8 Å to 12 Å.

According to this embodiment, the invention allows the removal in one same step of moisture and water as well as organic impurities such as pentafluoropropane (F245), 1,3,3,3-tetrafluoropropene (F1234ze), 1,3-dichloro-3,3-difluoropropene (F1232zd), 1,1-dichloro-3,3-difluoropropene (F1232za) or 1,1-dichloro-1,3,3-trifluoropropane (F243fc).

Preferably, the stream of 1-chloro-3,3,3-trifluoropropene is a stream of 1-chloro-3,3,3-trifluoropropene of E configuration (1233zd E). In this case, the 1-chloro-3,3,3-trifluoropropene of Z configuration (1233zd Z) can be considered to be an impurity completing the list of impurities mentioned above.

According to this embodiment, the initial hydrofluoroolefin stream (before the purifying and drying process) may comprise from 90% to 99% by weight of 1-chloro-3,3,3-trifluoropropene of E configuration (1233zd E), from 0.05% to 3% by weight of water, from 1% to 6% by weight of 1-chloro-3,3,3-trifluoropropene of Z configuration (1233zd Z), from 0.1% to 2% by weight of 1,3-dichloro-3,3-difluoropropene (F1232zd), from 0.05% to 2% by weight of pentafluoropropane (F245) and from 0.05% to 2% by weight of 1,1-dichloro-3,3-difluoropropene (F1232za), relative to the total weight of the hydrofluoroolefin stream.

According to one embodiment of the invention, the contacting step is performed at a temperature ranging from −20° C. to +80° C., preferably from +10° C. to +40° C., and under a pressure of 100 to 2200 kPa, preferably at atmospheric pressure.

According to one embodiment, the method of the invention is carried out in gas phase.

The present invention also concerns the use of an adsorbent in the meaning defined in the foregoing for simultaneous drying and purification of a stream of hydrofluoroolefins.

The characteristics detailed above concerning the method of the invention apply to the use according to the invention.

EXAMPLES

Example 1

Purification of a Stream of 1234yf 20 g of NK20® zeolite (type A having a pore diameter of 5 Å) available from CECA were placed in a reactor of length 70 cm and inner diameter of 1.6 cm; the 20 g of zeolite covered a height of about 16 cm in the reactor. The zeolite was previously dried under an inert gas at a flow rate of 20 l/h at 120° C. for 10 hours.

The purification test was then conducted at ambient temperature (25° C.) and at atmospheric pressure for a contact time of about 100 seconds and space velocity of 0.3 cm/s.

Several gas streams were tested and compared:
Stream 1: distilled 1234yf (98.64% purity) doped with 6,000 ppm by mass of F40.
Stream 2: crude product comprising 94.42% by weight of 1234yf and 245cb also comprising 8,300 ppm by mass of F40.
Stream 3: crude product comprising 94.55% by weight of 1234yf and 245cb also comprising 5,700 ppm by mass of F40, said crude product being subjected to a bubbling step in water at 18° C. to obtain a water-saturated gas stream (about 5,000 ppm by mass of water calculated from saturated vapour pressure).
Stream 4: crude product comprising 94.55% by weight of 1234yf and 245cb also comprising 4,700 ppm by mass of F40, said crude product being subjected to a bubbling step in water at 25° C. to obtain water-saturated gas stream (about 8,000 ppm by mass of water calculated from saturated vapour pressure).

For each test, the contact time was maintained until saturation of the zeolite. The impurities F40 were immediately removed from the gas stream to reach a content of less than 20 ppm by mass. Once the zeolite is saturated, the F40 content of the stream is again increased since said F40 can no longer be removed.

With this type of test, it is possible to evaluate the adsorption capacity of the zeolite expressed in g of F40 per 100 g of zeolite placed in the reactor.

The results are given in Table 1 below.

TABLE 1

Adsorption capacity of the molecular sieve NK20 ®

| Stream of 1234yf | | Contact time (s) | Time to saturation (h) | Adsorption capacity (%) |
|---|---|---|---|---|
| F40 | Moisture | | | |
| Stream 1 | 6,000 ppm | — | 100 | 40 | 5.1 |
| Stream 2 | 8,300 ppm | — | 121 | 37 | 4.4 |
| Stream 3 | 5,700 ppm | 5,000 ppm | 85 | 30 | 4.0 |
| Stream 4 | 4,700 ppm | 8,000 ppm | 100 | 29 | 3.3 |

The results in Table 1 show that streams 3 and 4 comprising quantities of moisture can be purified in the same manner as streams 1 and 2 not containing any detectable moisture. The adsorption capacities are respectively 4.0% and 3.3%, which effectively allows satisfactory purification of the organic impurities.

Example 2

Purification of a Stream of 1233zd (E Configuration)

Tests were conducted using 50 g of molecular sieve, and a crude stream of 1233zd E was placed in contact with the zeolite for 1 hour at a pressure of 0.5 bar and at ambient temperature (25° C.). The compositions of the ingoing and outgoing streams were compared. The molar proportions of each of the constituents were determined by gas chromatography analysis well known to persons skilled in the art.

Table 2 below gives the results obtained with a G5 zeolite (type X having a pore diameter of 10 Å) available from CECA. A test was also conducted with a stream of 1233zd E previously bubbled in water at 25° C.

TABLE 2 purification of 1233zd E

| Zeolite | G5 | | G5 (test with bubbling) | |
|---|---|---|---|---|
| Zeolite charge | 81 mL | | 81 mL | |
| Contacted 1233zd E | 57.6 g | | 58.4 g | |
| GC analysis | ingoing wt. % | outgoing wt. % | ingoing wt. % | outgoing wt. % |
| F1233zd E | 95.395 | 99.623 | 93.378 | 99.855 |
| F1233zd Z | 3.184 | 0.002 | 4.709 | — |
| F1234ze E | 0.176 | 0.222 | 0.012 | 0.019 |
| F1234ze Z | 0.090 | — | 0.034 | — |
| F245fa | 0.159 | — | 0.084 | — |
| F1232zd E | 0.627 | — | 1.241 | — |
| F243fc | 0.097 | — | 0.182 | — |
| F1232za | 0.134 | — | 0.271 | — |
| Other | 0.138 | 0.036 | 0.234 | 0.038 |

Table 2 above shows that a stream of 1233zd can be purified with an adsorbent such as a zeolite of X type.

Surprisingly the inventors have discovered that the test with the G5 zeolite in which the stream of 1233zd E comprises water (or moisture) allows purification of the stream and the subsequent obtaining of a stream of 1233zd E having improved purity.

Table 2 also shows that the method of the invention allows the separating of two isomers such as F1233zd E and F1233zd Z.

Table 2 also shows that with the method of the invention it is possible to remove F1234ze Z, whilst F1234ze E remains intact and is contained in the outgoing stream of F1233zd.

The invention claimed is:
1. A method for purifying and drying a hydrofluoroolefin stream comprising a stream of 2,3,3,3-tetrafluoro-1-propene (1234yf), water and impurities based on halogenated carbon compounds, the method comprising placing the hydrofluoroolefin stream in contact with an adsorbent, wherein the adsorbent is molecular sieves which comprise zeolites of type A having a pore diameter ranging from 3 Å to 6 Å, such that purification and drying are performed in one same step, wherein the impurities comprise one or more of chloromethane (F40), tetrafluoromethane (F14), trifluoromethane (F23), or 1,1-difluoroethane (F152a).

2. The method of claim 1, wherein the hydrofluoroolefin stream comprises at least 50% by weight of at least one same hydrofluoroolefin, relative to the total weight of the hydrofluoroolefin stream.

3. The method according to claim 1, wherein the hydrofluoroolefin stream comprises at least 70% by weight of at least one same hydrofluoroolefin, relative to the total weight of the hydrofluoroolefin stream.

4. The method of claim 1, wherein the impurities based on halogenated carbon compounds further comprise one or more of fluoromethane (F41), difluoromethane (F32), 1,1,1-trifluoroethane (F143 a), pentafluoroethane (F125), chloropentafluoroethane (F115), 1,1,1,2-tetrafluoroethane (F134a), pentafluoropropane (F245), monochlorotetrafluoropropene (F244), 1,3,3,3-tetrafluoropropene (F1234ze) isomer E or Z, 3,3,3-trifluoropropene (1243zf), 1,2,3,3,3-pentafluoropropene (F1225 ye), 3,3,3-trifluoropropyne, 1,3-dichloro-3,3-difluoropropene (F1232zd), 1,1-dichloro-3,3-difluoropropene (F1232za), 1,1-dichloro-1,3,3-trifluoropropane (F243fc), or cis isomer of 1-chloro-3,3,3-trifluoropropene (Z-1233zd).

5. A method for purifying and drying a hydrofluoroolefin stream comprising a stream of 1-chloro-3,3,3-trifluoropropene (1233zd), water and impurities based on halogenated carbon compounds, the method comprising placing the hydrofluoroolefin stream in contact with an adsorbent, wherein the adsorbent is a zeolite of type X having a pore diameter ranging from 8 Å to 12 Å, such that purification and drying are performed in one same step.

6. The method of claim 5, wherein the impurities comprise one or more of pentafluoropropane (F245), 1,3,3,3-tetrafluoropropene (F1234ze), 1,3-dichloro-3,3-difluoropropene (F1232zd), 1,1-dichloro-3,3-difluoropropene (F1232za), 1,1-dichloro-1,3,3-trifluoropropane (F243fc).

7. The method of claim 1, wherein the hydrofluoroolefin stream, before being placed in contact with the adsorbent, comprises from 10 to 10,000 ppm by mass of water.

8. The method of claim 1, wherein the hydrofluoroolefin stream, before being placed in contact with the adsorbent, comprises from 500 to 8,000 ppm by mass of impurities.

9. The method of claim 5, wherein the hydrofluoroolefin stream comprises at least 50% by weight of at least one same hydrofluoroolefin, relative to the total weight of the hydrofluoroolefin stream.

10. The method according to claim 5, wherein the hydrofluoroolefin stream comprises at least 70% by weight of at least one same hydrofluoroolefin, relative to the total weight of the hydrofluoroolefin stream.

11. The method of claim 5, wherein the impurities based on halogenated carbon compounds comprise one or more of chloromethane (F40), fluoromethane (F41), difluoromethane (F32), tetrafluoromethane (F14), trifluoromethane (F23), 1,1,1-trifluoroethane (F143a), 1,1-difluoroethane (F152a), pentafluoroethane (F125), chloropentafluoroethane (F115), 1,1,1,2-tetrafluoroethane (F134a), pentafluoropropane (F245), monochlorotetrafluoropropene (F244), 1,3,3,3-tetrafluoropropene (F1234ze) isomer E or Z, 3,3,3-trifluoropropene (1243zf), 1,2,3,3,3-pentafluoropropene (F1225ye), 3,3,3-trifluoropropyne, 1,3-dichloro-3,3-difluoropropene (F1232zd), 1,1-dichloro-3,3-difluoropropene (F1232za), 1,1-dichloro-1,3,3-trifluoropropane (F243fc), or cis isomer of 1-chloro-3,3,3-trifluoropropene (Z-1233zd).

12. The method of claim 5, wherein the hydrofluoroolefin stream, before being placed in contact with the adsorbent, comprises from 10 to 10,000 ppm by mass of water.

13. The method of claim 5, wherein the hydrofluoroolefin stream, before being placed in contact with the adsorbent, comprises from 500 to 8,000 ppm by mass of impurities.

* * * * *